(12) United States Patent
Weinzweig et al.

(10) Patent No.: US 7,953,260 B2
(45) Date of Patent: May 31, 2011

(54) PREDICTING MOVEMENT OF SOFT TISSUE OF THE FACE IN RESPONSE TO MOVEMENT OF UNDERLYING BONE

(75) Inventors: Jeffrey Weinzweig, Boston, MA (US); Darren Smith, New York, NY (US)

(73) Assignee: CranioSim Solutions, Inc., Highland Park, IL (US)

( * ) Notice: Subject to any disclaimer, the term of this patent is extended or adjusted under 35 U.S.C. 154(b) by 1002 days.

(21) Appl. No.: 11/450,651

(22) Filed: Jun. 9, 2006

(65) Prior Publication Data
US 2007/0299551 A1 Dec. 27, 2007

(51) Int. Cl.
G06K 9/00 (2006.01)
(52) U.S. Cl. ........................................ 382/128
(58) Field of Classification Search .................. 382/128, 382/154, 285
See application file for complete search history.

(56) References Cited

U.S. PATENT DOCUMENTS

| | | | |
|---|---|---|---|
| 4,600,919 A | 7/1986 | Stern | |
| 4,747,052 A | 5/1988 | Hishinuma et al. | |
| 4,835,712 A | 5/1989 | Drebin et al. | |
| 4,855,934 A | 8/1989 | Robinson | |
| 4,901,064 A | 2/1990 | Deering | |
| 4,905,233 A | 2/1990 | Cain et al. | |
| 5,124,914 A | 6/1992 | Grangeat | |
| 5,163,126 A | 11/1992 | Einkauf et al. | |
| 5,371,778 A | 12/1994 | Yanof et al. | |
| 5,611,030 A | 3/1997 | Stokes | |
| 5,731,819 A | 3/1998 | Gagne et al. | |
| 5,757,321 A | 5/1998 | Billyard | |
| 5,786,822 A | 7/1998 | Sakaibara | |
| 5,805,782 A | 9/1998 | Foran | |
| 5,809,219 A | 9/1998 | Pearce et al. | |
| 5,812,141 A | 9/1998 | Kamen et al. | |
| 5,847,712 A | 12/1998 | Salesin et al. | |
| 5,872,773 A | 2/1999 | Katzela et al. | |
| 5,881,243 A | 3/1999 | Zaumen et al. | |
| 5,894,308 A | 4/1999 | Isaacs | |
| 5,929,860 A | 7/1999 | Hoppe | |
| 5,933,148 A | 8/1999 | Oka et al. | |
| 5,949,969 A | 9/1999 | Suzuoki et al. | |
| 5,966,133 A | 10/1999 | Hoppe | |
| 5,966,134 A | 10/1999 | Arias | |
| 5,974,423 A | 10/1999 | Margolin | |
| 5,999,189 A | 12/1999 | Kajiya et al. | |
| 6,054,999 A | 4/2000 | Strandberg | |
| 6,057,859 A | 5/2000 | Handelman et al. | |
| 6,078,331 A | 6/2000 | Pulli et al. | |
| 6,098,107 A | 8/2000 | Narvarez-Guarnieri et al. | |
| 6,115,050 A | 9/2000 | Landau et al. | |

(Continued)

OTHER PUBLICATIONS

Altobelli, et al., "Computer-Assisted Three-Dimensional Planning in Craniofacial Surgery" *Plastic & Reconstructive Surgery*, 1993; 92(4):576-585; discussion 586-587.

(Continued)

*Primary Examiner* — Matthew C Bella
*Assistant Examiner* — Dennis Rosario
(74) *Attorney, Agent, or Firm* — Fish & Richardson P.C.

(57) ABSTRACT

Predicting movement of soft tissue of the face in response to movement of underlying bone includes storing, for first subjects, data identifying movement of soft tissue of the face in response to movement of underlying bone, and using the data to predict, for a second subject, movement of soft tissue of the face over time in response to movement of underlying bone.

36 Claims, 13 Drawing Sheets

U.S. PATENT DOCUMENTS

| | | | |
|---|---|---|---|
| 6,175,655 B1 | 1/2001 | George et al. | |
| 6,191,787 B1 | 2/2001 | Lu et al. | |
| 6,191,796 B1 | 2/2001 | Tarr | |
| 6,198,486 B1 | 3/2001 | Junkins et al. | |
| 6,201,549 B1 | 3/2001 | Bronskill | |
| 6,208,347 B1 | 3/2001 | Migdal et al. | |
| 6,219,070 B1 | 4/2001 | Baker et al. | |
| 6,239,808 B1 | 5/2001 | Kirk et al. | |
| 6,252,608 B1 | 6/2001 | Snyder et al. | |
| 6,262,737 B1 | 7/2001 | Li et al. | |
| 6,262,739 B1 | 7/2001 | Migdal et al. | |
| 6,292,192 B1 | 9/2001 | Moreton | |
| 6,292,194 B1 | 9/2001 | Powell, III | |
| 6,317,125 B1 | 11/2001 | Persson | |
| 6,337,880 B1 | 1/2002 | Cornog et al. | |
| 6,388,670 B2 | 5/2002 | Naka et al. | |
| 6,405,071 B1 | 6/2002 | Analoui | |
| 6,437,782 B1 | 8/2002 | Pieragostini et al. | |
| 6,478,680 B1 | 11/2002 | Yoshioka et al. | |
| 6,559,848 B2 | 5/2003 | O'Rourke | |
| 6,573,890 B1 | 6/2003 | Lengyel | |
| 6,593,924 B1 | 7/2003 | Lake et al. | |
| 6,593,927 B2 | 7/2003 | Horowitz et al. | |
| 6,608,627 B1 | 8/2003 | Marshall et al. | |
| 6,608,628 B1 | 8/2003 | Ross et al. | |
| 6,845,175 B2 * | 1/2005 | Kopelman et al. | 382/154 |
| 6,970,171 B2 | 11/2005 | Baraff et al. | |
| 7,050,904 B2 | 5/2006 | Powell et al. | |
| 7,292,716 B2 * | 11/2007 | Kim | 382/128 |
| 7,711,155 B1 | 5/2010 | Sharma et al. | 382/118 |
| 2001/0026278 A1 | 10/2001 | Arai et al. | |
| 2002/0035458 A1 * | 3/2002 | Kim et al. | 703/6 |
| 2002/0101421 A1 | 8/2002 | Pallister | |
| 2006/0018973 A1 * | 1/2006 | Kim et al. | 424/603 |
| 2007/0172155 A1 * | 7/2007 | Guckenberger | 382/305 |
| 2008/0159608 A1 * | 7/2008 | Suetens et al. | 382/128 |
| 2009/0237398 A1 | 9/2009 | Marshall et al. | |

OTHER PUBLICATIONS

Battagel, J.M. "The relationship between hard and soft tissue changes following treatment of Class II division I malocclusions using Edgewise and Fränkel appliance techniques" *European Journal of Orthodontics* 1990; 12(2):154-165.

Burgielski, et al., "Julius—A software framework for computer-aided-surgery" *Biomedizinische Technik*, 2002; 47 Suppl 1 Pt 1:101-3.

Eales, et al., "A Study of the accuracy of predicted soft tissue changes produced by a computer software package (COG 3.4) in a series of patients treated by the Le Fort I osteotomy" *British Journal of Oral & Maxillofacial Surgery* 1995; 33(6):362-369.

Ewing, et al., "Soft tissue response to mandibular advancement and genioplasty" *American Journal of Orthodontics & Dentofacial Orthopedics* 1992; 101(6):550-555.

Ferrario, et al., "Three-dimensional facial morphometric assessment of soft tissue changes after orthognathic surgery" *Oral Surg Oral Med Oral Pathol Oral Radiol Endod* 1999; 88:549-556.

Gateno, et al., "Three-Dimensional Surgical Planning for Maxillary and Midface Distraction Osteogenesis" *Journal of Craniofacial Surgery* 2003; 14(6):833-839.

Girod, et al., "Advances in interactive craniofacial surgery planning by 3D simulation and visualization" *International Journal of Oral & Maxillofacial Surgery* 1995; 24(1 Pt2):120-125.

Girod, et al., "Computer-aided 3-D simulation and prediction of craniofacial surgery: a new approach" *Journal of Cranio-Maxillofacial Surgery* 2001; 29(3):156-158.

Hack et al., "Long-term stability and prediction of soft tissue changes after LeFort I surgery" *American Journal of Orthodontics & Dentofacial Orthopedics* 1993; 104(6):544-555.

Hassfeld, et al., "Intraoperative guidance in maxillofacial and craniofacial surgery" *Proceedings of the Institution of Mechanical Engineers Part H—Journal of Engineering in Medicine* 1997: 277-283.

Hsieh, et al., "Virtual reality simulator for osteotomy and fusion involving the musculoskeletal system" *Computerized Medical Imaging and Graphics* 2002; 26(2):91-101.

Jans, et al., "Computer-Aided Craniofacial Surgical Planning Implemented in CAD Software" *Computer Aided Surgery* 1999; 4(3):117-128.

Keeve, et al., "Deformable Modeling of Facial tissue for Craniofacial Surgery Simulation" *Computer Aided Surgery* 1998; 3(5):228-238.

McCance, et al., "A three dimensional analysis of soft and hard tissue changes following bimaxillary orthognathic surgery in skeletal III patients" *British Journal of Oral & Maxillofacial Surgery* 1992; 30(5):305-312.

McCance, et al., "A three-dimensional analysis of bone and soft tissue to bone ratio of movements in 17 Skeletal II patients following orthognathic surgery" *European Journal of Orthodontics* 1993; 15(2):97-106.

Meehan, et al., "Three-dimensional simulation and prediction of craniofacial surgery" *Orthodontics & Craniofacial Research* 2003; 6 Suppl 1:102-107.

Papadopoulos, et al., "Three-dimensional craniofacial reconstruction imaging" *Oral Surgery, Oral Medicine, Oral Pathology; Oral Radiology, & Endodontics* 2002; 93(4)382-393.

Teschner, et al., "3-D Simulation of Craniofacial Surgical Procedures" *Studies in Health Technology & Informatics* 2001; 81:502-508.

Vannier, et al., "Three-Dimensional Imaging, Surgical Planning, and Image-Guided Therapy" *Radiologic Clinics of North America* 1996; 34(3):545-563.

Westermark, et al., "Three-Dimensional Osteotomy Planning in Maxillofacial Surgery Including Soft Tissue Prediction" *Journal of Craniofacial Surgery* 2005; 16(1):100-104.

"Advogato's Trust Metric", Retrieved from the Internet: URL<http://www.advogato.org/trust-metric.html> [retrieved on Nov. 18, 2010], (Feb. 2000).

"pmG Introduces Messiah: Animate 3.0", [online] Retrieved from the Internet: <URL:http://www.digitalproducer.com/aHTM/Articles/july_2000/july_17_00/pmg_intros_messiah_animate.htm> , 2 pgs., (Jul. 2000).

Alliez, et al., "Progressive Compression for Lossless Transmission of Triangle Meshes," University of Southern California, Los Angeles, CA, ACM SIGGRAPH, pp. 195-202, Aug. 2001.

Appel, Arthur, "The Notion of Quantitative Invisibility and the Machine Rendering of Solids." Proceedings of 22nd National Conference Association for Computing Machinery 1967.

Bajaj, et al., "Progressive Compression and Transmission of Arbitrary Triangular Meshes," Department of Computer Sciences, University of Texas at Austin, Austin TX, pp. 307-316, 1999.

Bandi et al., "Path Finding for Human Motion in Virtual Environments", Elsevier Science (2000).

Bandi et al., "Space Discretization for Efficient Human Navigation", Swiss Federal Inst. of Technology (1998).

Brockington, M., "Pawn Captures Wyvern: How Computer Chess Can Improve Your Pathfinding", Gama Network (2000).

Buck et al., "Performance-Driven Hand Drawn Animation", ACM (NPAR2000), pp. 101-108 (2000).

Catmull et al., "Recursively Generated B-Spline Surfaces on Arbitrary Topological Meshes," Computer Aided Geometric Design, 10(6):350-355 (1978).

Chow, "Optimized Geometry Compression for Real-time Rendering." Massachusetts Institute of Technology, Proceedings Visualization 1997, Oct. 19-24, 1997, Phoenix, AZ: 347-354.

Coelho et al., "An Algorithm for Intersecting and Trimming Parametric Meshes", ACM SIGGRAPH, pp. 1-8 (1998).

Cohen-Or, et al., "Progressive Compression of Arbitrary Triangular Meshes," Computer Science Department, School of Mathematical Sciences, Tel Aviv, Israel, Vis 99 IEEE Visualization, Oct. 1999.

Deering, M., "Geometry Compression," Computer Graphics. SIGGRAPH '95, pp. 13-20, 1995.

DeRose et al., "Subdivisional Surfaces in Character Animation", ACM, SIGGRAPH'98, pp. 85-94 (1998).

Dyn, N., Levin, D., and Gregory, J.A. "A Butterfly Subdivision Scheme for Surface Interpolation with Tension Control." ACM Transactions on Graphics, vol. 9, No. 2 (1990).

Egbert et al., "Collision-Free Object Movement Using Vector Fields", Brigham Young Univ., (1996).

Elber, "Line Art Rendering via a Coverage of Isoperimetric Curves." IEEE Trans. on Visualization and Computer Graphics, vol. 1, Dept. of Comp. Sci., Technion, Israel Inst. of Tech., Haifa, Israel (Sep. 1995).

Elber, Gershon, "Interactive Line Art Rendering of Freeform Surfaces", Eurographics'99, 18(3):C1-C12 (1999).

Foley et al., "Computer graphics: principal and practice." Addison-Wesley Publishing Company, Reading, MA, 1996: 1060-1064.

Frohlich et al., "Autonomous and Robust Navigation for Simulated Humanoid Characters in Virtual Environments", IEEE (2002).

Garcia-Luna-Aceves, "A Path-Finding Algorithm for Loop-Free Routing", IEEE (1997).

Garland et al., "Surface Simplification Using Quadratic Error Metrics", IEEE (1997).

Gooch et al., "A Non-Photorealistic Lighting Model for Automatic Technical Illustration," Computer Graphics Proceedings, Annual Conference Series, SIGGRAPH'98, pp. 447-452 (1998).

Gooch et al., "Interactive Technical Illustration," ACM Interactive 3D, pp. 31-38 (1999).

Heidrich et al., "Realistic, Hardware-Accelerated Shading and Lighting," ACM, (SIGGRAPH'99), pp. 171-178 (1999).

Hoppe, "Efficient Implementation of progressive meshes." Coput. & Graphics, vol. 22, No. 1: 27-36 (1998).

Hoppe, "Progressive Meshes," Microsoft Research: pp. 99-108, Web: http://www.research.microsoft.com/research/graphics/hoppe/, 1996 ACM-0-89791-746-4/96/008.

Hoppe, "View-Dependent Refinement of Progressive Meshes," Microsoft Research, Web: http://research.microsoft.com/~hoppe/, 1997.

Hoppe, H., "Hughes Hoppe's Home Page", [online] Retrieved from the Internet:<URL: http://research.microsoft.com/~hoppe/>, [retrieved on Nov. 16, 2005], (2005).

Hoppe, H., "Smooth View-Dependent Level-of-Detail Control and its Application to Terrain Rendering", IEEE Visualization (1998).

Kumar et al., "Interactive Display of Large Scale NURBS Models", ACM, Symp. on Interactive 3D Graphics, pp. 51-58 (1995).

Lake et al., "Stylized Rendering Techniques for Scalable Real-Time 3D Animation", NPAR, pp. 101-108 (2000).

Lander, Jeff, "Making Kine More Flexible,"Game Developer Magazine, 5 pgs., Nov. 1998.

Lander, Jeff, "Skin Them Bones," Game Developer Magazine, 4 pgs., May 1998.

Landsdown et al., "Expressive Rendering: A Review of Nonphotorealistic Techniques" IEEE Computer graphics and Applicatons: 29-37 (1995).

Lasseter, "Principles of Traditional Animation Applied to 3D Computer Animation" Pixar, San Rafael, California, 1987.

Lee, "Navigating through Triangle Meshes Implemented as Linear Quadtrees" Computer Science Department, Center for Automation Research, Institute for Advanced Computer Studies, University of Maryland College Park, MD, Apr. 1998.

Leung et al., "Interactive Viewing of 3D Terrain Models Using VRML", Syracuse Univ., (1998).

Lewis, "Pose Space Deformation: A Unified Approach to Shape Interpolation and Skeleton-Driven Deformation." Centropolis, New Orleans, LA, pp. 165-172, ACM 2000 1-58113-208-5/00/07.

Lonzano-Perez et al., "An Algorithm for Planning Collision-Free Paths Among Polyhedral Obstacles", ACM (1979).

Ma et al., "Extracting Feature Lines for 3D Unstructured Grids" Institute for Computer Applications in Science and Engineering (ICASE), NASA Langley Research Center, Hampton, VA, IEEE (1997).

Markosian, et al., "Real-Time Nonphotorealistic Rendering," Brown University site of the NSF Science and Technology Center for Computer Graphics and Scientific Visualization, Providence, RI, 1997.

Pajarola et al., "Compressed Progressive Meshes" Graphics, Visualization & Usability Center, College of Computing, Georgia Institute of Technology, Jan. 1999.

Pedersen, "A Framework for Interactive Texturing on Curved Surfaces", ACM, pp. 295-301 (1996).

Popovic, et al., "Progressive Simplicial Complexes," ACM SIGGRAPH 1997 Conference Proceedings.

Pueyo, X. et al., "Rendering Techniques '96," Proc. of Eurographics Rendering Workshop 1996, Eurographics, pp. 61-70 (1996).

Raskar, "Image Precision Silhouette Edges" University of North Carolina at Chapel Hill, Microsoft Research, 1999 Symposium on Interactive 3D Graphics Atlanta, GA: 135-231 (1999).

Rockwood, A. et al., "Real-time Rendering of Trimmed Surfaces," Computer Graphics (SIGGRAPH '89 Proceedings) 23:107-116 (1989).

Samet, "Applications of spatial data structures: computer graphics, image processing, and GIS." University of Maryland, Addison-Wesley Publishing Company, Reading, MA: 1060-1064 (Jun. 1990).

Sousa, M., et al., "Computer-Generated Graphite Pencil Rendering of 3-D Polygonal Models", Eurographics'99, 18(3):C195-C207 (1999).

Stam, J., "Exact Evaluation of Catmull-Clark Subdivision Surfaces at Arbitrary Parameter Values", SIGGRAPH 98 Conference Proceedings, Annual Conference Series, pp. 395-404 (1998).

Taubin et al., "3D Geometry Compression", SIGGRAPH'98 Course Notes (1998).

Taubin, et al., "Progressive Forest Split Compression," IBM T.J. Watson Research Center, Yorktown Heights, NY, 1998.

Thalmann et al., "Computer Animation in Future Technologies", Univ. of Geneva (1996).

Thomas et al., "The Illusion of Life: Disney Animation," Hyperion, 3:47-71, New York, NY (1984).

To et al., "A Method for Progressive and Selective Transmission of Multi-Resolution Models", ACM (1999).

Ware et al., "Layout for Visualizing Large Software Structures in 3D", Univ. of New Brunswick (2000).

Wilhelms, J. & Van Gelder, A., "Anatomically Based Modeling," Univ. California Santa Cruz [online], 1997 [retrieved Dec. 22, 2004], retrieved from the Internet: <URL: http://graphics.stanford.edu/courses/cs448-01-spring/papers/wilhelms.pdf>.

Zeleznik et al., "Sketch: An Interface for Sketching 3D Scenes." Brown University site of the NSF Science and Technology Center for Computer Graphics and Scientific Visualization (1996).

Zorin, D., Schroeder, P., and Sweldens, W. "Interpolating Subdivision for Meshes of Arbitrary Topology." Tech. Rep. CS-TR-96-06, Caltech, Department of Computer Science, (1996).

* cited by examiner

PREDICTING MOVEMENT OF SOFT TISSUE OF THE FACE IN RESPONSE TO MOVEMENT OF UNDERLYING BONE

TECHNICAL FIELD

This patent application relates generally to predicting movement of soft tissue of the face in response to movement of underlying bone.

BACKGROUND

Craniofacial surgery is a term used to describe surgery involving the bones of the face and skull (craniofacial skeleton), as well as the soft tissue of the face. This type of surgery requires skill and precision, particularly in procedures that involve reconstructing a patient's facial features. In such procedures, a slight miscalculation can result in an unacceptable facial asymmetry and require complex corrective surgery.

Craniofacial surgeons must therefore attempt to predict how a patient will heal and, in a pediatric patient, grow, and tailor their surgical techniques accordingly. This can be difficult, particularly in cases involving movement of underlying bone. More specifically, as might be expected, movement of underlying bone will cause overlying soft tissue (e.g., skin) also to move. Post-surgical conditions such as swelling and scarring can affect that movement. In time, these conditions resolve, and the soft tissue settles or re-drapes into its final position. However, resolution of post-surgical conditions varies for different patients, and is dependent on a number of factors. As a result, the soft tissue may not settle or re-drape as predicted.

In addition to the foregoing post-surgical conditions, other factors can affect movement of the soft tissue. For example, patients with taut skin, such as younger patients and those who have had previous surgery, are likely to exhibit more pronounced soft tissue movement, whereas patients with loose skin, such as the elderly, are likely to exhibit less pronounced soft tissue movement. Similarly, patients with relatively thick skin, excessive pre-existing scarring, and skin conditions, such as scleroderma, will exhibit soft tissue movement that is dependent, at least in part, on their skin type and/or skin condition. These factors can also increase the difficultly of predicting the final position of soft tissue following craniofacial surgery.

SUMMARY

This patent application describes methods and apparatus, including computer program products, to predict movement of soft tissue over time in response to movement of an underlying structure, e.g., bone of the craniofacial skeleton.

In general, a process for predicting of movement of soft tissue may include one or more of the following: providing, accessing, obtaining or storing, for first subjects, data identifying movement of soft tissue of a face in response to movement of underlying bone, and using the data to predict, for a second subject, movement of soft tissue of a face over time in response to movement of underlying bone. The foregoing process may also include one or more of the following features.

The data may take into account one or more biophysical properties that affect movement of the soft tissue. The one or more biophysical properties may include pliability of the soft tissue, thickness of the soft tissue, and scar tissue associated with the soft tissue. The data may take into account an amount of time that lapses between movement of the underlying bone and movement of the soft tissue.

Using the data to predict movement of the soft tissue for the second subject may include generating a graphical model of the second subject, where the graphical model simulates the soft tissue and the underlying bone for the second subject to thereby display simulated soft tissue and simulated underlying bone, moving the simulated underlying bone on the graphical model, and displaying, via the graphical model, movement of the simulated soft tissue in response to movement of the simulated underlying bone. The data may be used to characterize movement of the simulated soft tissue. Displaying movement may include displaying positions of the simulated soft tissue at different times following movement of the underlying bone. Movement of the underlying bone may be a result of craniofacial surgery performed on the second subject. The foregoing process may be used to predict soft tissue movement based on movement of underlying structures other than bone including, but not limited to, implants and hard tissue, such as cartilage.

In general, a process for predicting of movement of soft tissue may include one or more of the following: obtaining imaging scans for a patient, where the imaging scans relate to craniofacial anatomy of the patient, obtaining first data and second data from the imaging scans, where the first data corresponds to bone and the second data corresponds to skin, integrating the first data and the second data to generate a graphical model of the patient, where the graphical model comprises a model of the skin and a model of the bone, and using recorded data and the graphical model to predict movement of skin in response to movement of bone, where the recorded data specifies, for past subjects, how skin moves in response to movement of underlying bone. The foregoing process may also include one or more of the following features.

Using the recorded data to predict movement of skin may include relating the graphical model of the skin to the graphical model of the bone through the recorded data. Relating the graphical model of the skin to the graphical model of the bone may include relating movement of the graphical model of the skin to movement of the graphical model of the bone. Movement of the graphical model of the skin may be displayed in response to movement of the graphical model of the bone in order to predict movement of skin in response to movement of bone. A portion of bone represented by the graphical model may be moved, and a portion of skin represented by the graphical model may be moved in response to movement of the bone. The portion of skin may be moved in accordance with the recorded data. The portion of skin may comprise a window of skin within a predefined radius (or other dimension) of the portion of bone that has been moved.

Movement of skin and bone may simulate movement of the skin and bone during surgery (or other medical procedures). The process further may also include displaying a position of the portion of skin at specified times following surgery, where the specified times are defined by the recorded data, and the position of the portion of skin is defined by the recorded data. The portion of skin may move in accordance with a ratio (or other relationship) of skin movement to bone movement. The ratio may be defined based on a location of the portion of skin as it relates to craniofacial anatomy.

In general, a process for predicting of movement of soft tissue may include one or more of the following: maintaining a database containing data for past subjects, where data for each past subject specifies how skin moves over time in response to movement of underlying bone. The skin and underlying bone may comprise parts of a craniofacial anatomy, and the data in the database may be usable by a graphics program to predict skin movement for a current subject in response to movement of underlying bone. The process may also include obtaining updates to the database, and incorporating the updates into the database to thereby produce an updated database. The updates may comprise data for additional subjects that specifies how skin moves over time in response to movement of underlying bone. The updates may enhance an ability of the graphics program to predict skin movement in response to movement of underlying bone. The foregoing process may also include one or more of the following features.

Obtaining the updates may include receiving the updates over a computer network. The foregoing process may also include providing only physicians who have obtained subscriptions with access to the updated database.

In general, a process for predicting of movement of soft tissue may include one or more of the following: providing, accessing, obtaining or storing, for first subjects, data identifying movement of soft tissue in response to movement of an underlying structure, and using the data to predict, for a second subject, movement of soft tissue over time in response to movement of an underlying structure. The underlying structure for the first subjects may include implants, and the underlying structure for the second subject may include an implant. The underlying structure for the first subjects may include bone, and the underlying structure for the second subject may include bone.

The foregoing processes may affect treatment of a patient. For example, a therapy, such as a surgical procedure, may be selected for the second subject based on the predicted movement of soft tissue. Likewise, a surgeon may select between two courses of action, e.g., before or during surgery, based on the predicted movement of soft tissue. The two courses of action may include, e.g., moving a bone to one position or to another, selecting a size and/or shape or site of an implant, and the like.

In other implementations, prediction of movement of soft tissue may occur at a first site, e.g., a first healthcare facility, and results of the prediction may be transferred, e.g., over a computer network such as the Internet, to a second site, e.g., a second healthcare facility where a surgeon responsible for the patient is resident.

The details of one or more examples are set forth in the accompanying drawings and the description below. Further features, aspects, and advantages of the invention will become apparent from the description, the drawings, and the claims.

DESCRIPTION OF THE DRAWINGS

Like reference numerals in different figures indicate like elements.

DETAILED DESCRIPTION

Figure 1:
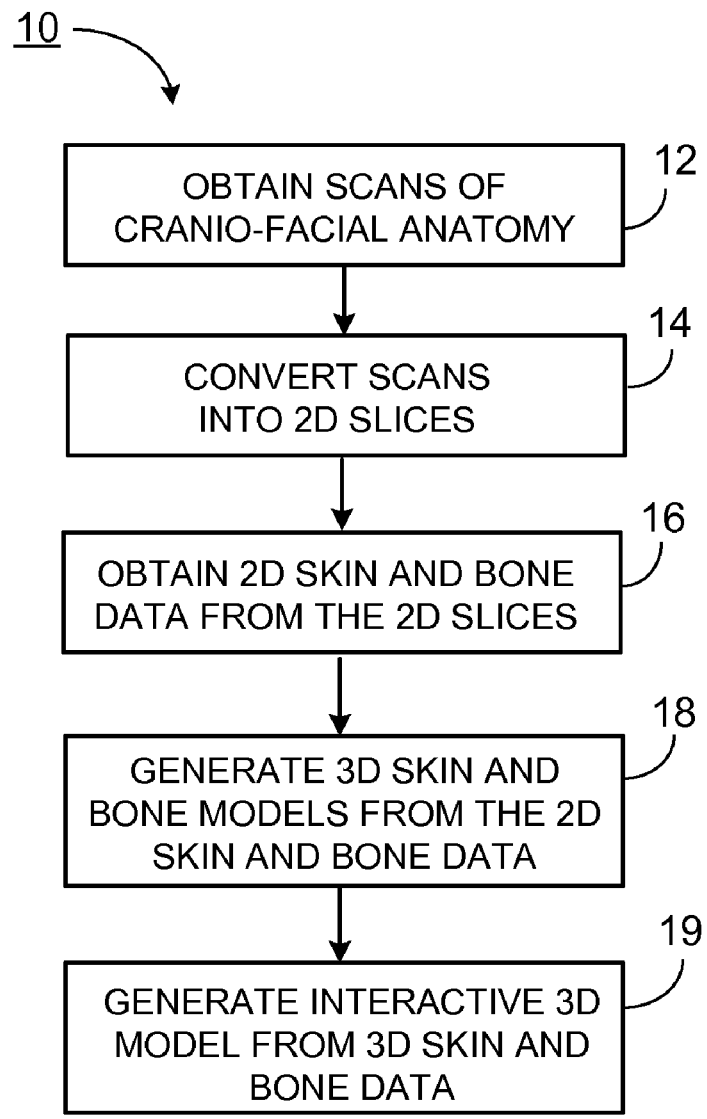
FIG. 1 is a flowchart showing a process for generating a graphical model of a patient, which is used for predicting relative movement of skin and bone.

Described below are processes for predicting movement of soft tissue in response to movement of an underlying hard structure, such as (but not limited to) bone. In this context, soft tissue may include, but is not limited to, skin and underlying tissue, such as fat and muscle. The processes predict movement of the soft tissue (e.g., of the face) using a three-dimensional (3D) graphical model of a current patient and a database containing information for previous patients. The information for each previous patient specifies, among other things, how that patient's skin moved over time in response to movement of underlying bone of the craniofacial skeleton. The graphical model uses this previous patient data to predict, and to display, how the current patient's skin will react over time in response to movement of underlying bone. A description of the database is set forth below, followed by a description of the graphical model.

The database may include records identifying bones of the craniofacial skeleton, or portions thereof, and specifying movement associated with such bones. The records may also identify skin and soft tissue that are affected by movement of the bones, and specify movement of the skin and soft tissue, over time, resulting from movement of these bones. For example, a database record may identify movement of a jaw bone by three millimeters in a particular direction, along with corresponding movement of affected skin a week after surgery, three months after surgery, six months after surgery, one year after surgery, etc.

The bones may be identified by name and/or by a location. In one implementation, a CT scan may be obtained for each patient, and the resulting 3D model may be aligned along the ear rods on a 3D XYZ grid. Both the bones and skin may be identified in the database using 3D XYZ coordinates. For instance, a database record may identify a target bone by name and/or by XYZ coordinate.

The record may also contain the XYZ coordinates of overlying skin that is affected by movement of the target bone. The skin may be part of a predefined window that identifies skin affected by movement of the target bone. The amount of movement that qualifies a particular tract of skin for inclusion in the window may be designated beforehand. Various factors may also be taken into account when defining the window. For example, some areas of skin may be relatively tight, necessitating a relatively small window, whereas other areas of skin may be relatively loose, necessitating a larger window. Clinical information may be used to aid in defining such windows.

Each record may also identify characteristics that are specific to the patient or skin in an affected area. For example, a record may contain information on a patient's age, sex, race, build, skin type, and the existence and type of bone fracture(s). Anything that may affect a patient's skin may be incorporated into the database. For instance, biophysical properties, such as skin thickness or pliability, and/or medical conditions, such as skin diseases and pre-existing scarring, also affect how a patient's skin will react to underlying bone movement. Therefore, this information may also be in the database.

Magnitude and/or direction of movement of the bones and skin may be defined in the database. In the foregoing example, a database record for movement of a jaw bone by three millimeters may contain 3D XYZ coordinates identifying the bone or portion thereof, 3D XYZ coordinates specifying the window of skin affected by the movement, and data specifying the direction and amount of movement of the bone and of skin in the window at various times following surgery (e.g., shortly thereafter, three months after, six months after, one year after, etc.). As noted above, the database record may also include information on how other factors may affect skin movement.

Regarding movement of the skin, it is noted that movement of underlying bone may affect different areas of skin in the window differently. For example, pulling a bone outwardly from a patient's face will have a greater effect on skin directly overlying the bone than on skin at the periphery of the bone. The database takes this into account by assigning appropriate movement to different parts of skin in the window. In one implementation, the data specifying the direction and amount of movement of the skin and bone is based on centroids. That is, skin at the center of motion of the bone is assigned a greater range of motion than skin radiating out from the center of motion. Additionally, motion vectors may be incorporated to define skin movement.

The database may be generated using clinical data obtained from previous surgeries. For example, each time a craniofacial surgeon performs an operation, the surgeon may record both pre-operative and post-operative data. The pre-operative data may include the locations of the affected skin and bone prior to surgery, along with other information, such as the patient's age, sex, race, etc., which are set forth above. The post-operative data may include the positions of the bone and skin shortly after surgery and at periodic intervals thereafter. The intervals may vary based on the type of surgery. As noted, examples of intervals that may be used include, but are not limited to, three months, six months, nine months, and one year after surgery.

Figure 7:
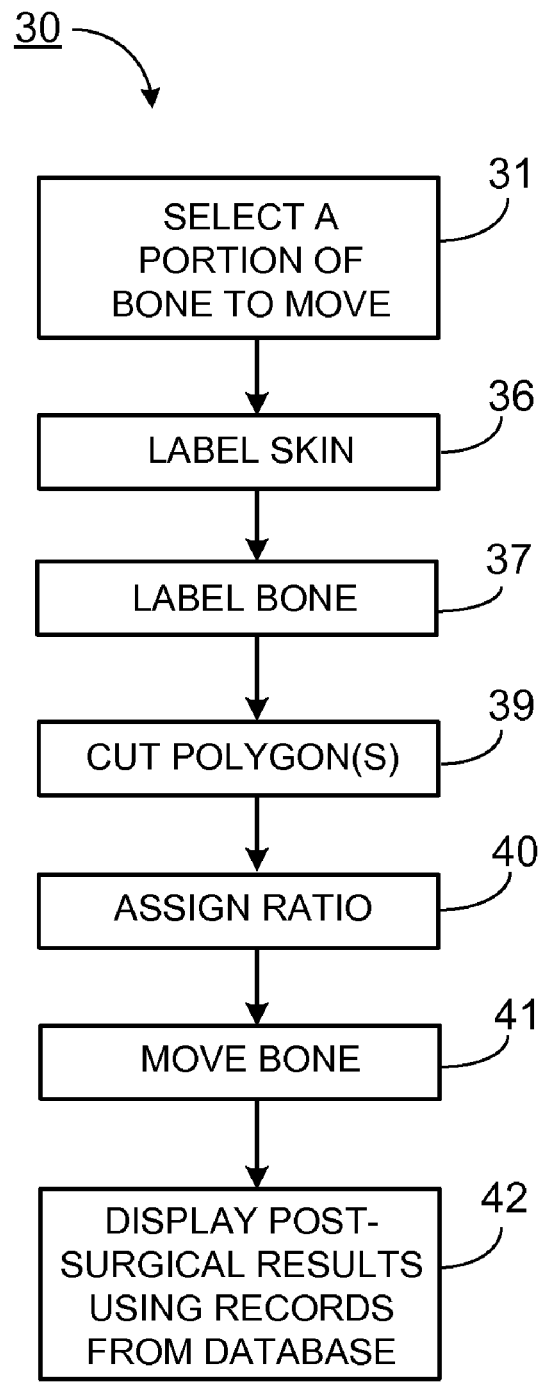
FIG. 7 is a flowchart showing a process for performing simulated surgery on the graphical representation of the skull shown in FIG. 5.

A computer program associated with the database may receive the foregoing clinical information, store the information at appropriate locations of the database, and calculate any necessary parameters needed to make the information usable by process 30 (see FIG. 7). For example, the computer program may calculate a skin-movement-to-bone-movement ratio for each record. This ratio may relate movement of skin to movement of bone while taking into account all information in a particular record. The database may be updated, as described below, each time a surgeon performs an operation. Generally speaking, the updates to the database enhance the ability to predict skin movement in response to movement of underlying bone. That is, the more information that the database contains, the more information there is to draw upon in predicting, for future patients, movement of skin in response to movement of bone.

Referring now to FIG. 1, process 10 may be performed using the foregoing database to predict movement of soft tissue of the craniofacial skeleton over time in response to movement of underlying bone. To begin, process 10 obtains (12) scans of a patient's craniofacial anatomy. The scans may be computerized tomography (CT) scans. CT scans are sometimes referred to as "CAT" scans, but CT will be used herein. Use of CT scans is advantageous because CT scans are almost always taken prior to surgery and thereafter, and, therefore, specialized scanning for process 10 is not required. Data obtained via CT scans is 3D data. For example, the 3D data may be, but need not be, voxels. Other 3D or N-dimensional ($N \geqq 3$) data may be used.

Figure 2A:
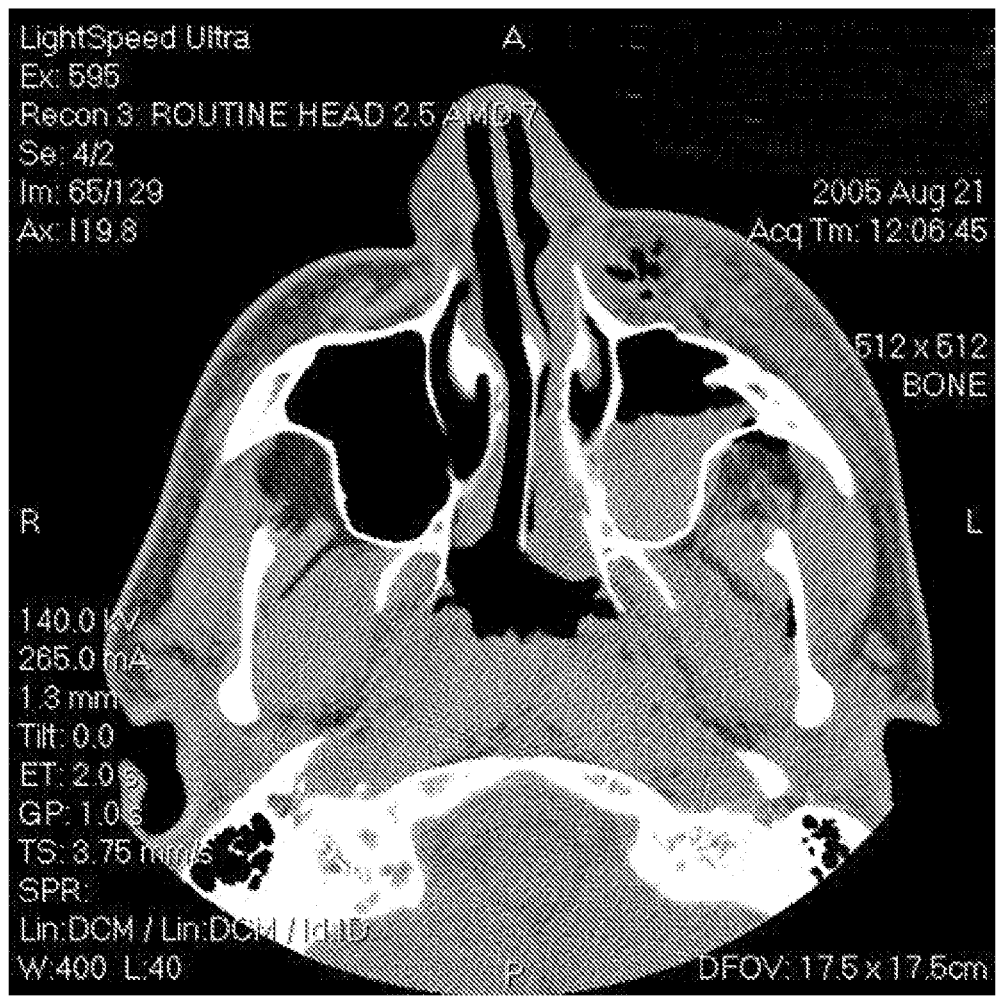
FIGS. 2a to 2c show two-dimensional slices obtained from a CT scan.
Figure 2B:
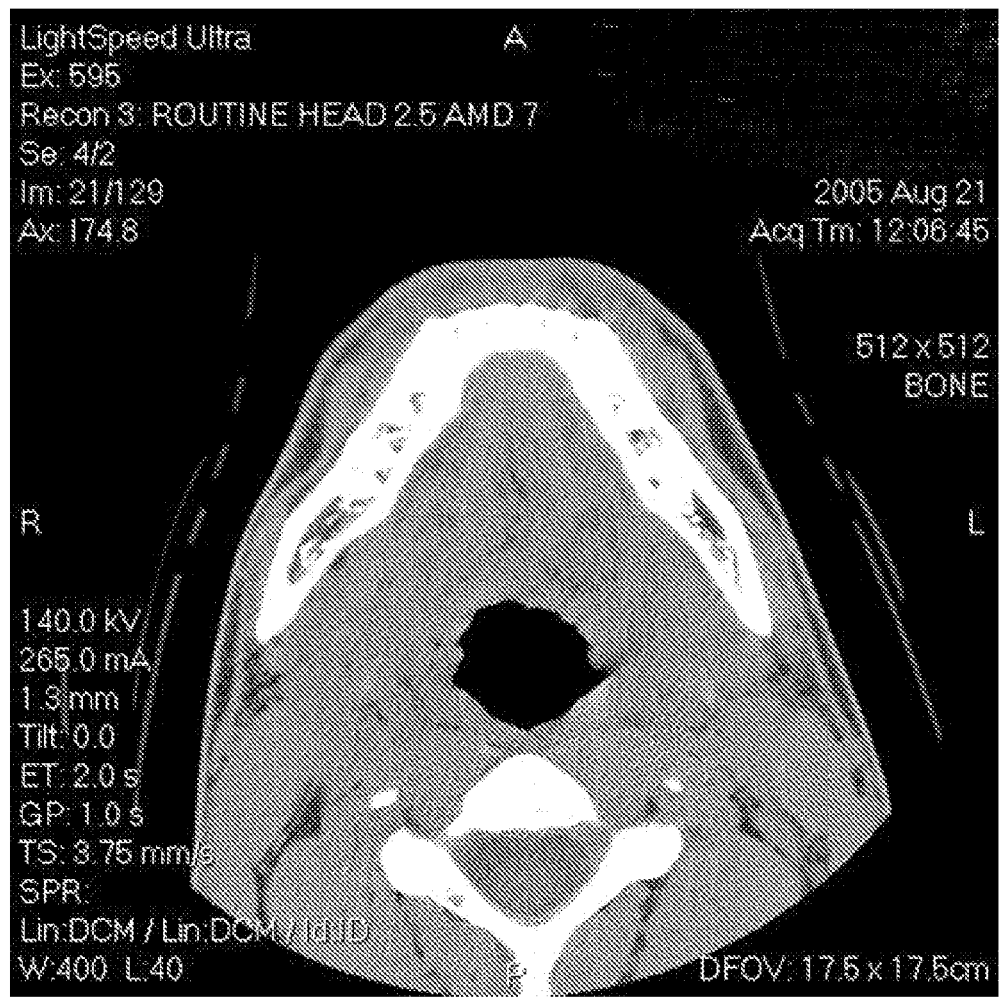
Figure 2C:
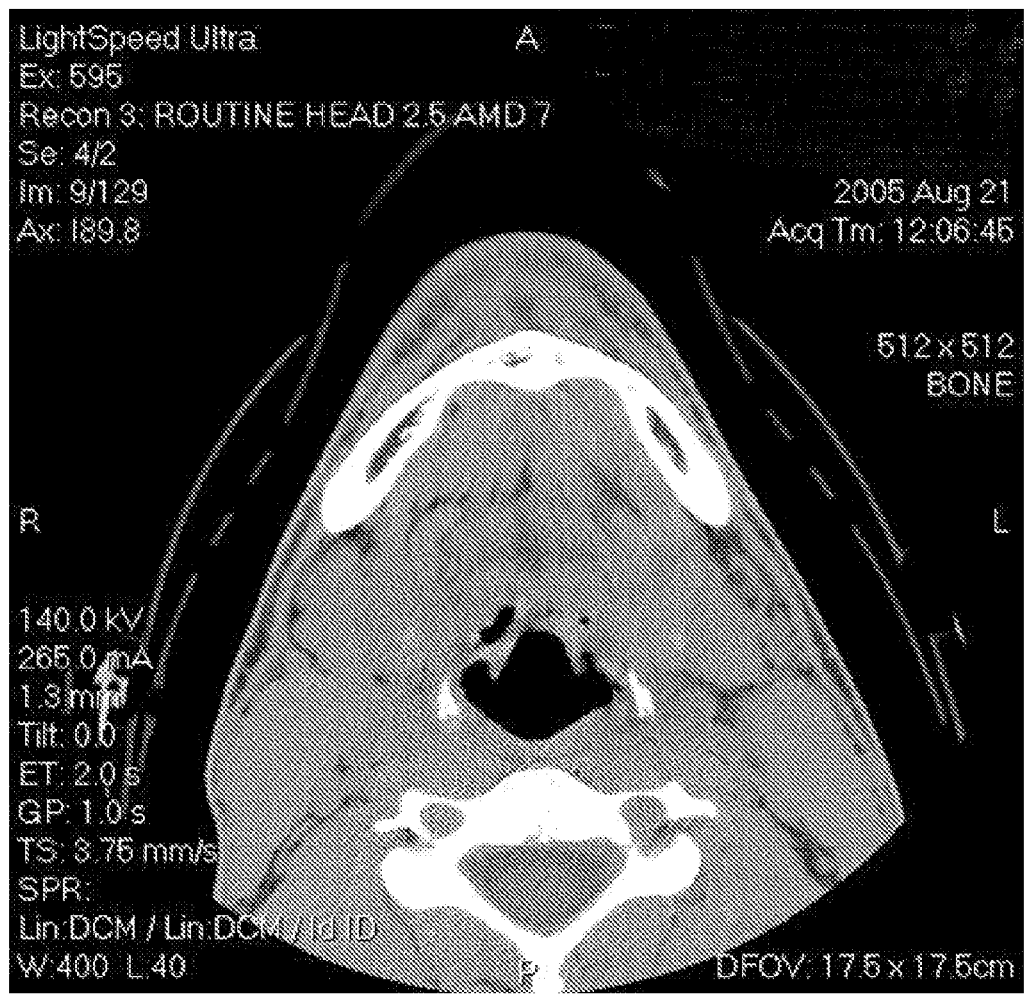

According to process 10, the 3D data resulting from the CT scan is converted (14) into two-dimensional (2D) slices, such as the slices shown in FIGS. 2a to 2c. The 2D slices are 2D representations of the patient, which are typically taken at intervals along the horizontal, vertical, or coronal axis of the patient's head. Each 2D slice shows both hard and soft tissue. The hard and soft tissue is depicted using varying grayscale values, with white representing the most dense tissue such as bone, with darker colors representing soft tissue (less dense) such as skin and muscle, and with black indicating an absence of tissue.

Figure 10A:
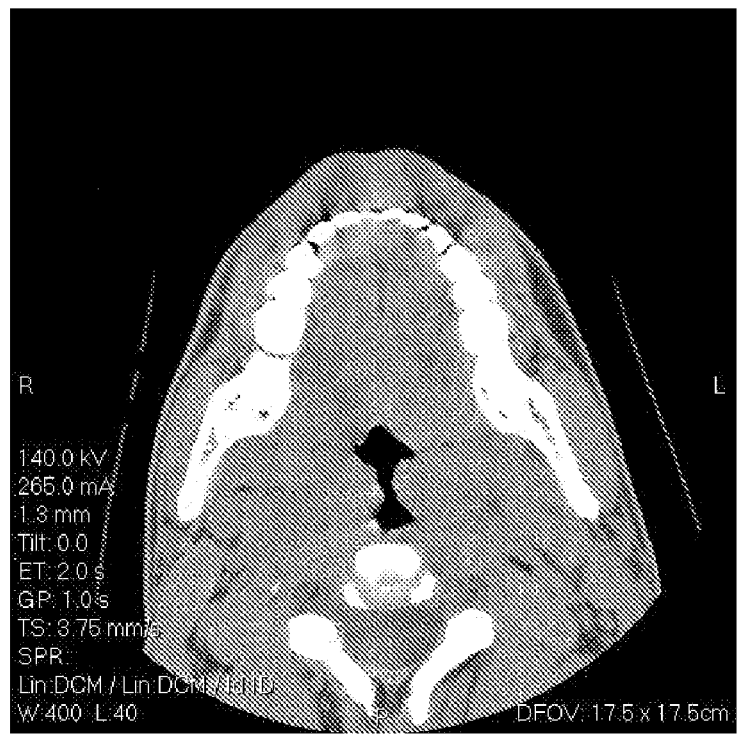
FIGS. 10a to 10c show, graphically, processing of CT scans to detect skin.
Figure 10B:
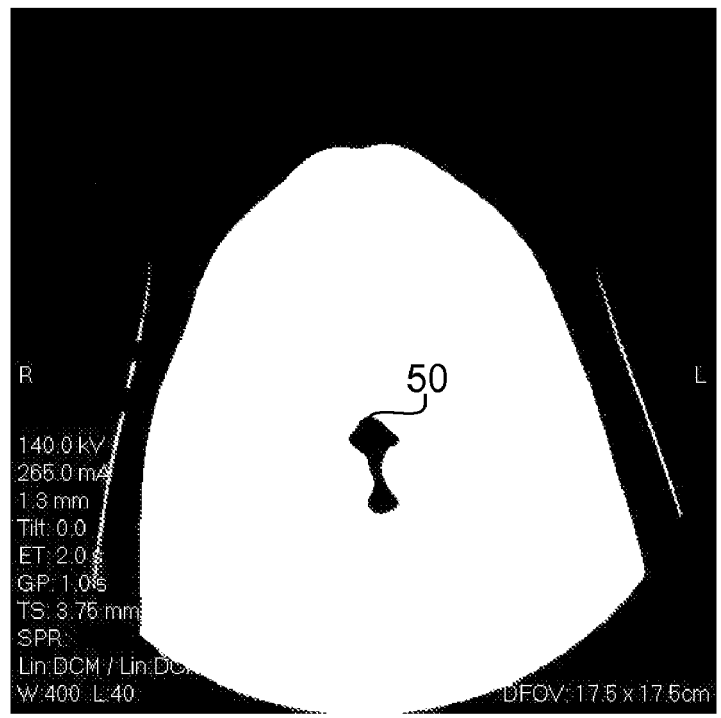
Figure 10C:
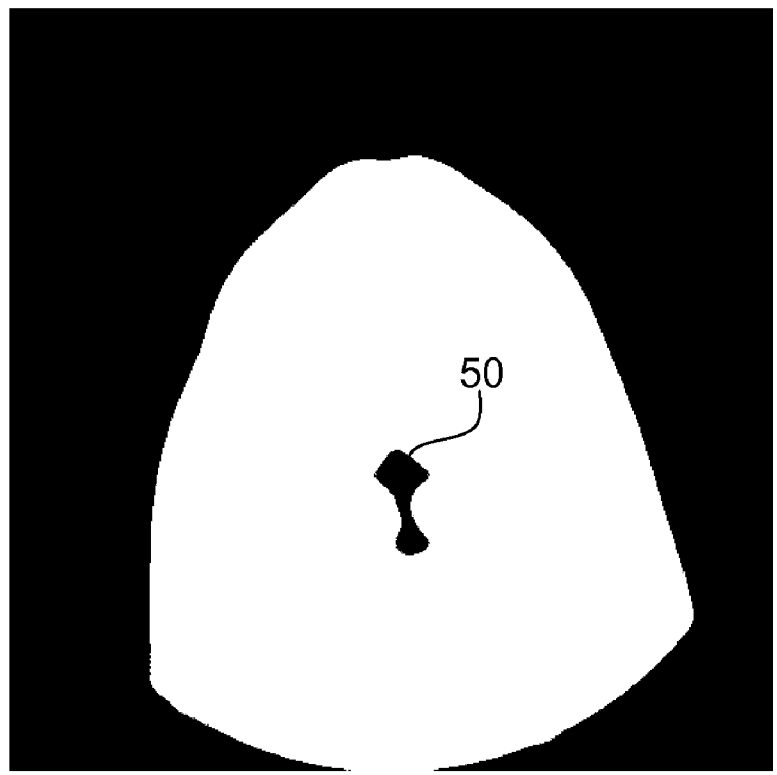

Process 10 obtains (16) 2D bone data and 2D skin data from the 2D slices. The bone data identifies bone in the 2D slices and the skin data identifies skin in the 2D slices. Commercially-available software, such as Adobe® Photoshop® may be used to obtain the 2D skin data and 2D bone data using the 2D slices. For example, the 2D bone data may be identified by its color, i.e., white. Accordingly, all white areas may be selected in a 2D slice and extracted from the 2D slice, thereby obtaining 2D bone data for the 2D slice. Skin, however, has the same, or similar, shading as muscle. As a result, some additional processing is required to identify skin data in the 2D slices. In this regard, skin is different from muscle in that skin borders the black background. The additional processing takes advantage of this fact to isolate the skin from the background, and thereby generate 2D skin data. Referring to FIG. 10a, an axial CT scan is shown. In FIG. 10b, soft tissue is selected and then converted to white using color range criteria. In FIG. 10c, all non-white pixels are converted to black. Although not shown in the figures, all internal black (e.g., 50) may be deleted. Software identifies the resulting white/black border as a surface boundary corresponding to skin. The thickness of the skin may be specified in software or may be selected by a user.

The 2D skin and 2D bone data generated by Photoshop®, or other image processing software, may be stored prior to further processing. Macros may be written for Adobe® Photoshop® (or whatever graphics program is used to extract the skin and bone data) to obtain the 2D skin and 2D bone data in the manner described above. The CT images may be batch processed by such macros, thereby reducing the amount of time needed to generate the 2D skin and 2D bone data. This process may also include the direct extraction of 3D surfaces from the CT data.

The original CT images are registered relative to pre-defined reference points. The 2D skin data and 2D bone data preserve this registration. Thus, when the 2D skin data and 2D bone data are recombined in the 3D graphical mode (or simply, 3D model) described below, the 3D model maintains the original physical relationship between skin and bone. In this regard, process 10 integrates the 2D skin and 2D bone data to generate a 3D model for the patient. To this end, process 10 generates (18), from the 2D skin and 2D bone data, separate 3D models that simulate the patient's skin and bone. These separate 3D models together define a graphical model that represents the patient. The 3D models may be generated using any type of software that accepts 2D images, such as the 2D skin and 2D bone data, and that generates 3D models from those 2D images (or, again, the 3D data may be directly extracted from CT data).

Figure 3:
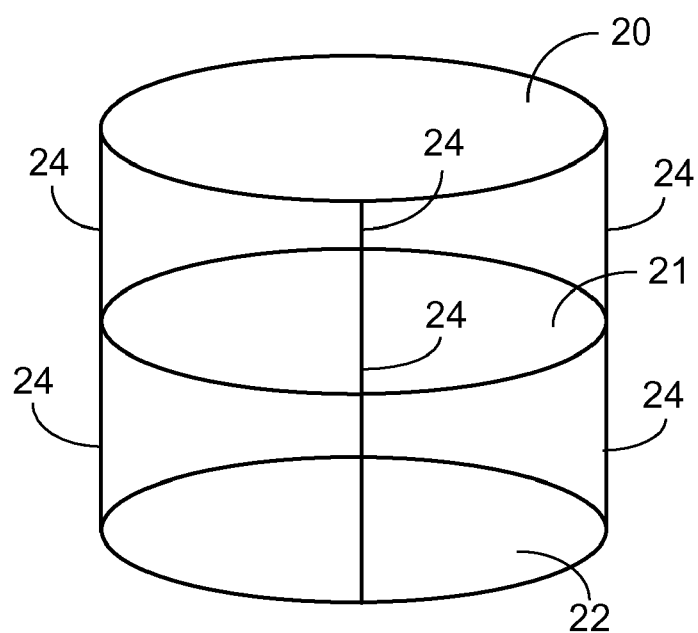
FIG. 3 shows the generation of a three-dimensional model from two-dimensional slices.

In this implementation, process 10 uses Amira™, from Mercury Computer Systems®, to generate 3D models of the patient's skin and bone from the 2D skin and 2D bone data. To begin, the 2D bone data and the 2D skin data produced via Photoshop® are input to Amira™. Amira™ generates a 3D model of the patient's craniofacial bone structure from the 2D bone data, and generates a separate 3D model of the overlying skin from the 2D skin data. Techniques for generating 3D models from 2D slices are well-known. One technique is illustrated in FIG. 3. As shown in FIG. 3, slices 20 to 22 are arranged in order (each slice is typically numbered sequentially). The ordered slices are related by forming connections 24, e.g., lines, between corresponding points on the slices. Once a shell is formed for the 3D model, 3D graphics polygons are generated.

Figure 4:
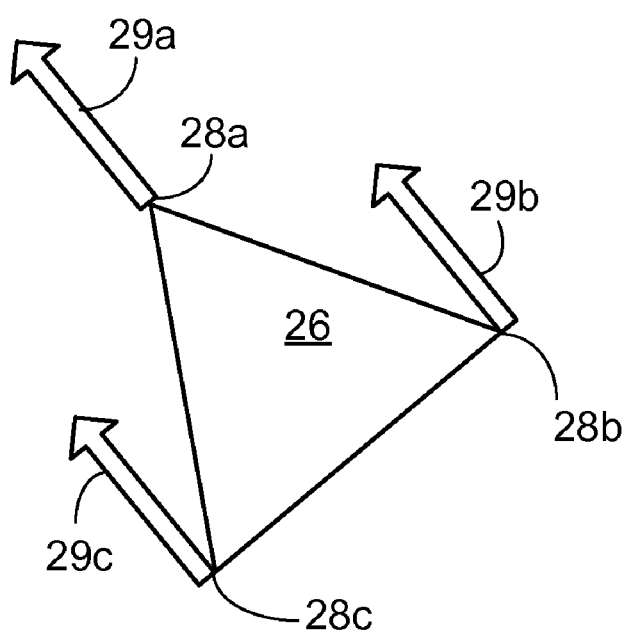
FIG. 4 is a block diagram of a polygon used in three-dimensional graphics data.
Figure 5:
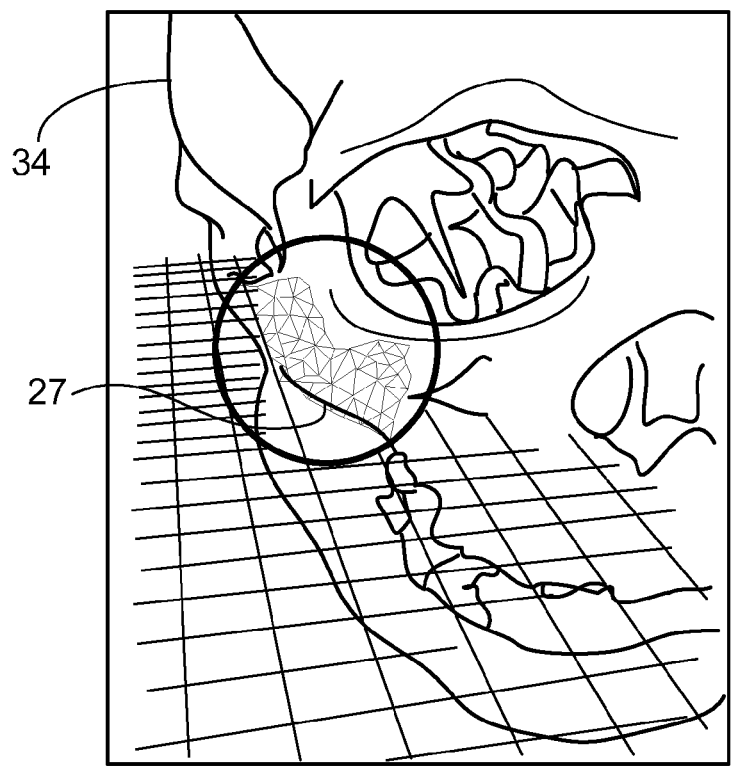
FIG. 5 is a screen shot showing a graphical representation of a patient's skull.

As shown in FIG. 4, 3D data for a polygon 26 includes coordinates for three vertices 28a, 28b, 28c positioned in Cartesian XYZ (or other) space. These vertices define a face and edges for the polygon. A unit normal vector (normal) 29a, 29b, 29c at each corresponding vertex affects how the vertex is perceived relative to a predefined reference point in the virtual world that a 3D model inhabits. FIG. 5 shows examples of polygons 27 that simulate a portion of the patient's skull. Corresponding skin polygons are not shown in FIG. 5. Instead, the remainder of the patient's skull (in FIG. 5) and the patient's skin (in FIG. 6) are shown shaded. It is noted, however, that the shading is applied over the polygons, i.e., the polygons are there.

The 3D models generated by Amira™, or similar program(s), may be stored prior to further processing. Process 10 employs the 3D graphics program Maya®, or similar program(s), to generate (19) an interactive 3D model of the craniofacial anatomy of the patient from the 3D skin model and the 3D bone model generated by Amira™, or similar program(s). This portion of process 10 may be implemented in conjunction with a software plug-in to Maya®, similar commercial program(s), or as an independent program. To provide a distinction from standard Maya®, the Maya® platform enhanced with the software plug-in will henceforth be referred to as "the predictor".

Figure 6:
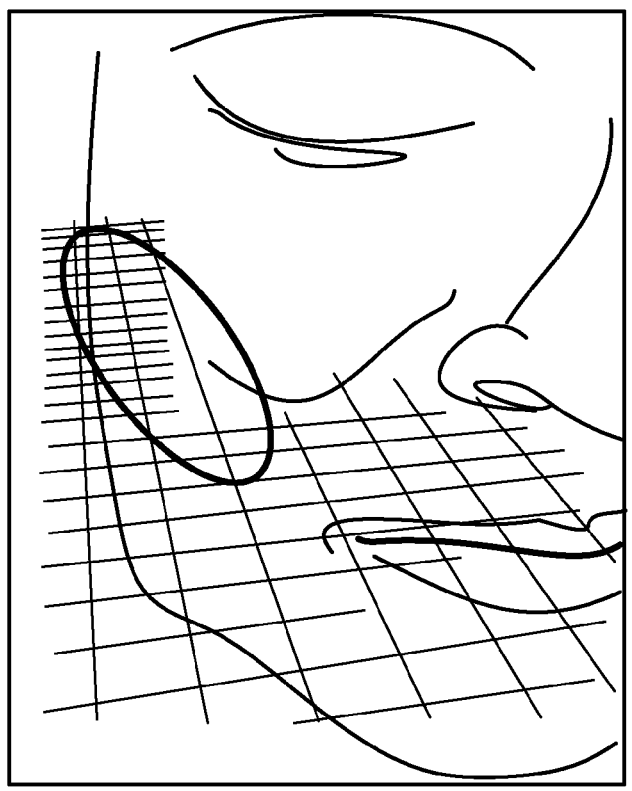
FIG. 6 is a screen shot showing a graphical representation of the patient's facial soft tissue, i.e., the skin and soft tissue on the head that overlies the facial bones of the skull.

The Maya® platform enables selection and display of the 3D skin model and the 3D bone model, as shown in FIGS. 5 and 6. The predictor relates the 3D skin model to the 3D bone model physically using the biomechanical information from the CT scans. The predictor relates the 3D skin model and the 3D bone model functionally through user inputs and records retrieved from the database. Through the information in these records, the predictor is able to display movement of overlying skin as a function of the movement of underlying bone, and to display movement of the skin over time. This movement constitutes a prediction of how the patient's real skin and bone will behave.

As explained below, a physician (or, more generally, a user) may be prompted by the predictor to select various criteria to describe the patient. For example, the user may be prompted to select the patient's age, sex, race, build, skin type, the existence and type of bone fracture(s), and/or medical history. The predictor, in conjunction with Maya®, allows a user to select a portion of bone from the 3D bone model, and to move that portion of bone on-screen in order to simulate surgical operation on the bone. Using the input criteria and the selected portion of bone, the predictor is able to extract a record from the database that most accurately predicts movement of the skin and bone. The predictor, in conjunction with Maya®, then implements the movement specified by that database record on the 3D skin model of the patient.

As noted, movement of the skin on the 3D skin model may be displayed at specified points in time, such as a week after surgery, three months after surgery, six months after surgery, and one year after surgery. Other intervals may be selected depending upon the information available from the database. If the database does not contain information for a particular interval, the predictor may perform an interpolation in order to obtain the requested data. Thus, if the database contains information for skin movement after six months and for skin movement after one year, and a physician would like to know skin movement for nine months, the predictor may interpolate between the six-month and one-year data to obtain an approximation of skin movement for the nine-month period.

FIG. 7 shows a process 30 by which a user and the predictor interact to simulate movement of soft tissue of the face using the patient's graphical model, i.e., the 3D skin and 3D bone models. Process 30 may follow, or be incorporated into, process 10. Referring to FIGS. 5 to 7, a user selects (31) a portion 27 of a bone to move in 3D bone model 34, along with skin associated with the bone. This is done using standard interactive Maya tools, which enable selection of polygons corresponding to the bone. Selection of the polygons is depicted graphically in FIG. 5. Thereafter, the user labels (36) the 3D skin model as skin by clicking on the 3D skin model and identifying it as such. The cutting and subsequent movement may be performed using standard Maya tools. The user labels (37) the 3D bone model as bone by clicking on the 3D bone model and identifying it as such. The user cuts (39) the selected polygons corresponding to the bone, which are referred to as a "polygonal subset", thereby simulating a surgical incision on the bone that the polygonal subset represents.

The predictor determines which vertices on the skin model will be affected by bone movement using information from the database. Process 30 assigns (40), to the vertices of the affected skin model, a ratio of skin movement to bone movement. This ratio corresponds to the amount of movement expected for a particular tract of skin (the polygonal subset), as set forth in the database. As explained above, some tracts of skin exhibit more movement than others in response to movement of underlying bone. For example, skin near the nose exhibits less movement than skin over the cheek. By assigning a ratio, the user is effectively defining the amount of movement expected for a particular tract of skin. Nose skin, for example, may be assigned a lower ratio than cheek skin to reflect that nose skin moves less in response to underlying bone movement than cheek skin.

The ratios may be predefined, e.g., in the database. That is, the predictor may provide the user with a list of possible ratios, from which the user may select an appropriate ratio for a tract of skin under consideration. Alternatively, the ratio may be automatically assigned. The ratios may correlate to predefined skin tracts, such as nose skin, cheek skin, chin skin, forehead skin and the like. The ratios may also take into account other factors that affect skin movement, including those stored in the database, namely age, sex, race, build, skin type, medical history, and the like. If the tract of skin under consideration is between one of the predefined tracts, the user may instruct the predictor to perform an interpolation between two existing ratios. The interpolation may be a simple average or a more complex type of interpolation. In some implementations, the predictor may also offer extrapolation as an option in lieu of, or in addition to, interpolation.

Figure 8:
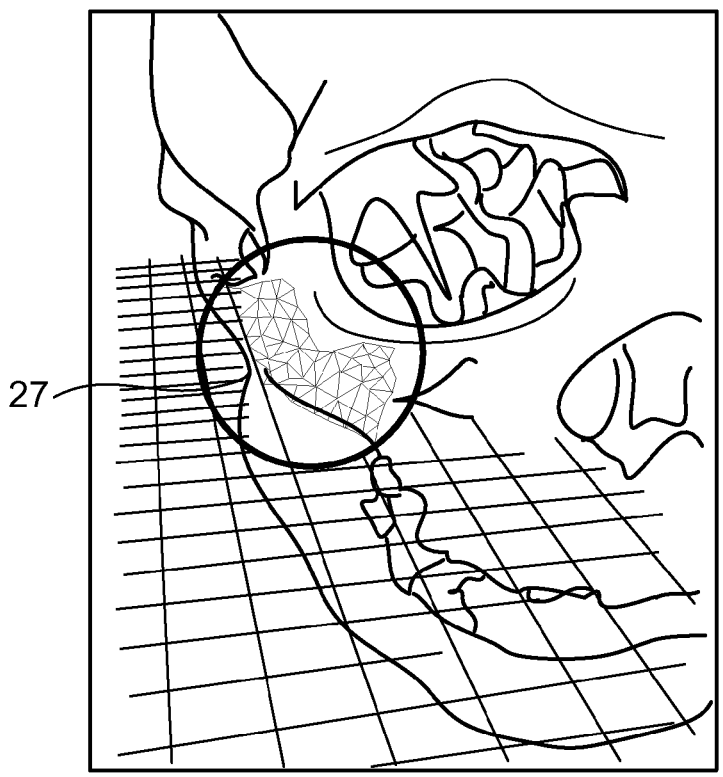
FIG. 8 is a screen shot showing a graphical representation of the patient's skull following the simulated surgery of FIG. 7.
Figure 9:
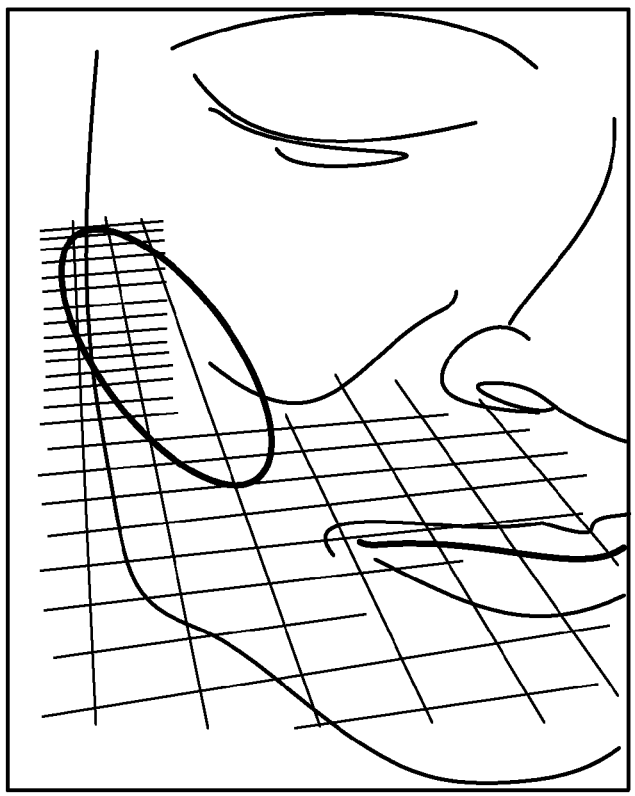
FIG. 9 is a screen shot showing a graphical representation of the patient's skin over the skull following the simulated surgery of FIG. 7.
Figure 11A:
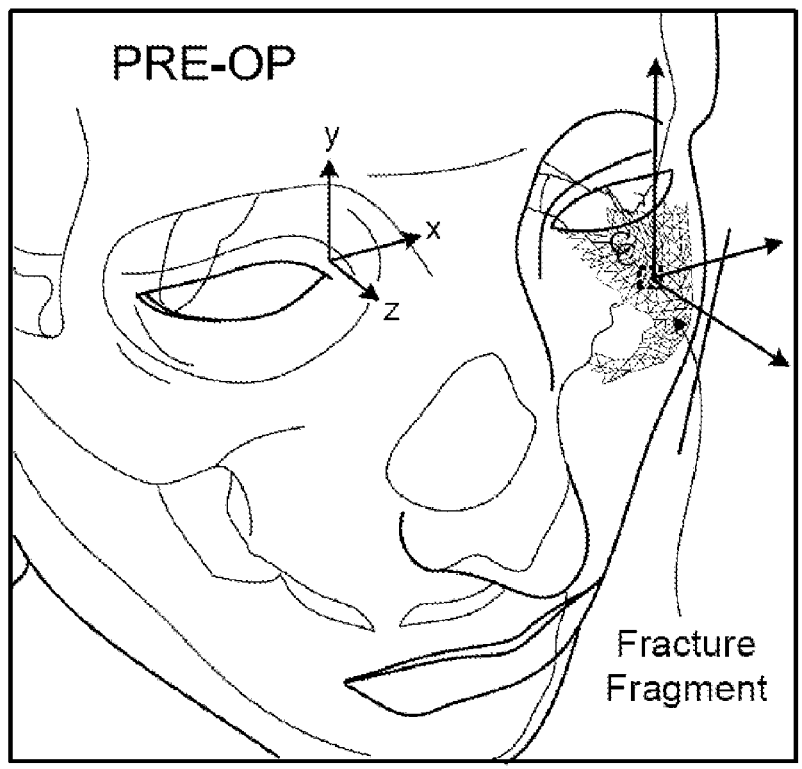
FIGS. 11a to 11d show graphical representations of a patient's skin at a pre-operative stage (11a), at an immediate post-operative stage (11b), at three months after surgery (11c), and at nine months after surgery (11d).
Figure 11B:
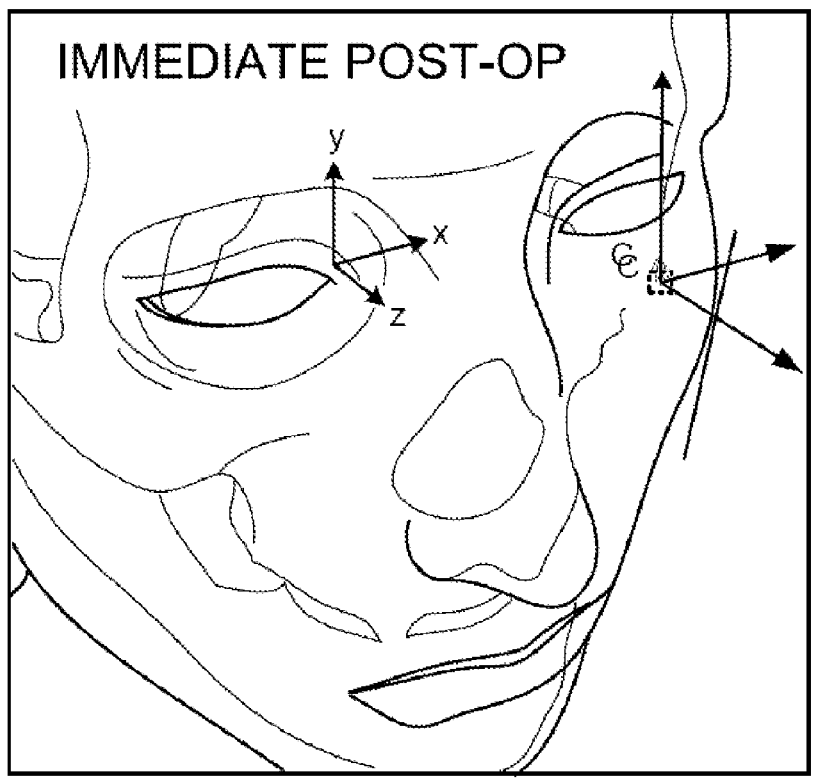
Figure 11C:
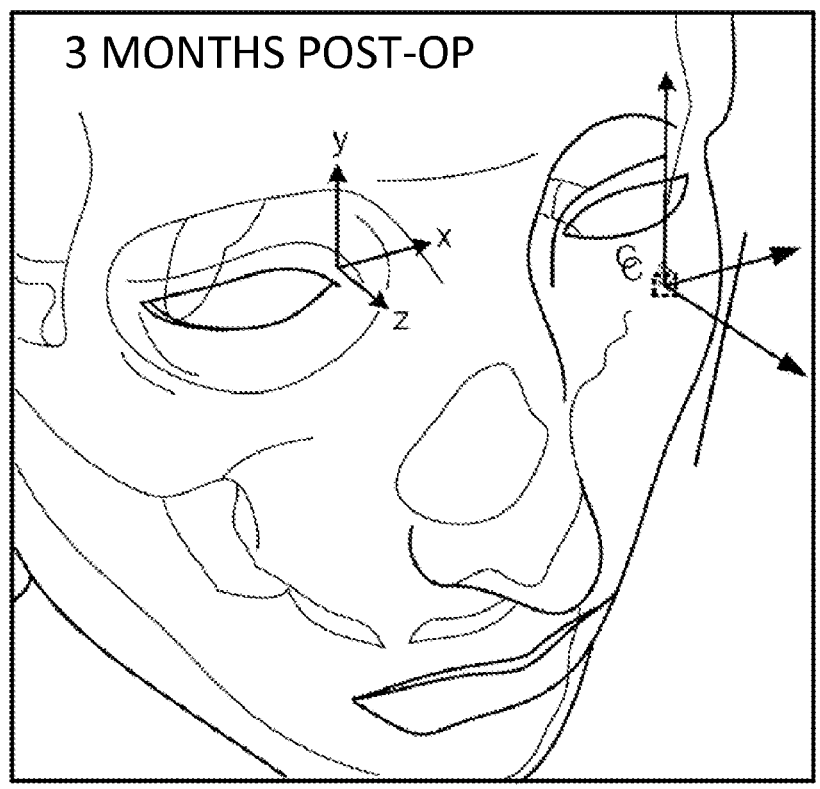
Figure 11D:
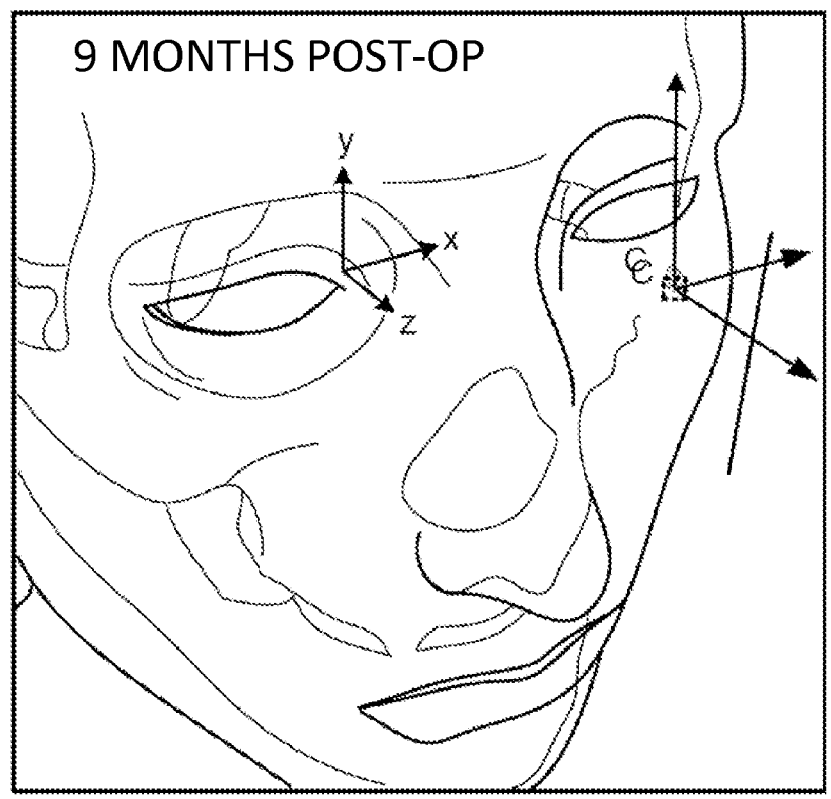

Once the ratios have been assigned, the user moves (41) the selected portion of bone to simulate actual bone movement during surgery. This is shown in FIG. 8. The affected skin moves based on the movement of the bone, and in accordance with the ratio specified by the user. The predicted immediate post-surgical result is displayed to the user, as shown in FIG. 9. Thereafter, the user may instruct the predictor to display (42) post-surgical result predictions at various time periods. For example, the user may instruct the predictor to display the result at three months after surgery. In response, the predictor retrieves the appropriate record(s) from the database, and modifies graphical model of FIG. 9 according to those records. More specifically, the predictor modifies the skin movement based on the information in the database records (which, as noted above, reflects clinical observations of past subjects). FIG. 11a shows an example of a graphical representation of a patient's skin at a pre-operative stage; FIG. 11b shows an example of a graphical representation of a patient's skin at an immediate post-operative stage; FIG. 11c an example of shows a graphical representation of a patient's skin at three months after surgery; and FIG. 11d shows an example of a graphical representation of a patient's skin at nine months after surgery.

The user may instruct the predictor to display the results at a time period for which there is no data in the database. For example, as explained above, if the database contains information for skin movement after six months and for skin movement after one year, and a physician would like to know skin movement for nine months, the predictor may interpolate between the six-month and one-year data to obtain an approximation of skin movement for the nine-month period. In some implementations, the predictor may also extrapolate data using past subject data from the database. For example, the predictor may extrapolate skin movement following a one-year period based on information in the database the describes skin movement, e.g., up to nine months.

All or part of the processes described herein and their various modifications (hereinafter referred to as "the processes") can be implemented, at least in part, via a computer program product, i.e., a computer program tangibly embodied in one or more information carriers, e.g., in one or more machine-readable storage media, for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more mass storage devices for storing data, e.g., magnetic, magneto-optical disks, or optical disks. Information carriers suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

The processes may be used in conjunction with any type of craniofacial surgery including, but not limited to, reconstructive surgery, cosmetic surgery, surgery to correct birth defects, post-traumatic surgery, and orthognathic surgery (surgery on the jaws). The processes may also be used outside the context of craniofacial surgery. That is, the processes are not limited to use with predicting movement of soft tissue of the face, but rather may be used to predict movement of any bodily soft tissue provided that an appropriate database is available to provide past patient data.

Similarly, processes 10 and 30 are not limited to predicting movement of overlying soft tissue in response to movement of underlying bone. Rather, the processes may be used to predict movement of soft tissue in response to movement of any underlying structure, including, but not limited to, other tissues, organs, or foreign substances being inserted into the body. In one example, processes 10 and 30 may be used to predict movement of soft tissue of the face in response to insertion of a facial implant, such as high-density porous polyethylene (Medpor®), manufactured by Porex®. Examples of implants include, but are not limited to, breast implants, cheek implants, jaw implants, and skin implants. Thus, processes 10 and 30 can be particularly beneficial to plastic surgeons in their work. Likewise, processes 10 and 30 may be used in conjunction with tissue expanders in order to predict soft tissue movement in response to operation of a tissue expander.

The processes are not limited to the hardware and software described herein. For example, laser scans, ultrasound, magnetic resonance imaging (MRI), or any other suitable imaging scan may be used in place of, or in addition to, CT scans for skin models. The processes may be stand-alone and/or may be implemented with or without one or more commercially-available programs, e.g., Maya®, Amira™, Photoshop® or others.

The processes may be implemented in software that is installed directly onto a user's personal computer (PC) or they may be Web-based. In their Web-based implementations, the functionality of the processes, and accessibility to the associated database, may be provided by a Web server, which is accessible to a client, such as the user's PC, over the Internet or other network. Using this model, physicians may provide updates to the database from remote locations. These updates may be solicited by the owner of the database either directly or over the Internet. For instance, the owner of the database may request database information from participating physicians and, in response, the owner may provide the physicians with access to information in the database. Alternatively, physicians wishing to use the updated database may be required to subscribe to (i.e., pay for) a service that provides periodic updates to a database stored on the physician's system, or that provides access to a periodically updated central database.

The actions shown above in the processes may be performed in a different order, and/or one or more actions may be omitted.

Elements of different implementations described herein may be combined to form other implementations not specifically set forth above. Other implementations not specifically described herein are also within the scope of the following claims.

What is claimed is:

1. A method performed by one or more processing devices, comprising:
   storing, in memory and for first subjects, first three-dimensional (3D) data identifying movement of soft tissue of a face in response to movement of underlying bone; and
   predicting, using at least some of the first 3D data movement of soft tissue of a face of a second subject over time in response to movement of underlying bone, the first subjects and the second subject comprising different people;
   wherein predicting movement of the soft tissue of the face of the second subject is performed by the one or more processing devices and comprises:
      generating a graphical model of the second subject using second 3D data for soft tissue and underlying bone of the second subject, the graphical model simulating the soft tissue and the underlying bone for the second subject to thereby display simulated soft tissue and simulated underlying bone;
      moving the simulated underlying bone on the graphical model; and
      displaying, via the graphical model, movement of the simulated soft tissue in response to movement of the simulated underlying bone, the at least some of first 3D data being used to predict movement of the simulated soft tissue for the second subject, wherein the graphical model is displayed via a computer.

2. The method of claim 1, wherein the first 3D data takes into account one or more biophysical properties that affect movement of the soft tissue, the one or more biophysical properties including pliability of the skin, thickness of the soft tissue, and scar tissue associated with the soft tissue.

3. The method of claim 1, wherein the first 3D data takes into account an amount of time that lapses between movement of the underlying bone and movement of the soft tissue.

4. The method of claim 1, wherein displaying comprises displaying positions of the simulated soft tissue at different times following movement of the underlying bone.

5. The method of claim 1, wherein movement of the underlying bone is a result of craniofacial surgery performed on the second subject.

6. The method of claim 1, wherein generating the graphical model of the second subject comprises:
   obtaining imaging scans for the second subject, the imaging scans relating to craniofacial anatomy of the second subject;
   obtaining first data and second data from the imaging scans, the first data corresponding to bone and the second data corresponding to soft tissue, the first data and the second data corresponding to the second 3D data;
   integrating the first data and the second data to generate the graphical model.

7. The method of claim 1, wherein displaying comprises displaying a position of the simulated soft tissue at specified times following surgery, the specified times being defined by recorded data.

8. The method of claim 1, wherein the simulated soft tissue moves in accordance with a ratio of skin movement to bone movement, the ratio being defined based on a location of the soft tissue as the location relates to craniofacial anatomy.

9. The method of claim 1, further comprising:
   maintaining a database containing the first 3D data, the database being in the memory;
   obtaining updates to the database; and
   incorporating the updates into the database to thereby produce an updated database, the updates comprising additional 3D data for additional subjects that specifies how soft tissue moves over time in response to movement of underlying bone.

10. The method of claim 9, wherein obtaining the updates comprises receiving the updates over a computer network.

11. The method of claim 9, further comprising providing only physicians who have obtained subscriptions with access to the updated database.

12. The method of claim 1, further comprising:
   predicting, using at least some of the first 3D data, movement of soft tissue of the second subject over time in response to movement of an underlying structure that is not bone.

13. One or more non-transitory machine-readable storage media comprising instructions that are executable to cause one or more processing devices to:
   store, in memory and for first subjects, first three-dimensional (3D) data identifying movement of soft tissue of a face in response to movement of underlying bone; and
   predict, using at least some of the first 3D data, movement of soft tissue of a face of a second subject over time in response to movement of underlying bone, the first subjects and the second subject comprising different people;
   wherein predicting movement of the soft tissue of the face of second subject comprises:
      generating a graphical model of the second subject using second 3D data for soft tissue and underlying bone of the second subject, the graphical model simulating the soft tissue and the underlying bone for the second subject to thereby display simulated soft tissue and simulated underlying bone;
      moving the simulated underlying bone on the graphical model; and
      displaying, via the graphical model, movement of the simulated soft tissue in response to movement of the simulated underlying bone, the at least some of first 3D data being used to predict movement of the simulated soft tissue for the second subject.

14. The one or more machine-readable storage media of claim 13, wherein the first 3D data takes into account one or more biophysical properties that affect movement of the skin, the one or more biophysical properties including pliability of the skin, thickness of the skin, and scar tissue associated with the skin.

15. The one or more machine-readable storage media of claim 13, wherein the first 3D data takes into account an amount of time that lapses between movement of the underlying bone and movement of the soft tissue.

16. The one or more machine-readable storage media of claim 13, wherein displaying comprises displaying positions of the simulated soft tissue at different times following movement of the underlying bone.

17. The one or more machine-readable storage media of claim 13, wherein movement of the underlying bone is a result of craniofacial surgery performed on the second subject.

18. The one or more machine-readable storage media of claim 13, wherein instructions to generating the graphical model comprise instructions that are executable to cause one or more processing devices to:

obtain imaging scans for the second subject, the imaging scans relating to craniofacial anatomy of the second subject;

obtain first data and second data from the imaging scans, the first data corresponding to bone and the second data corresponding to soft tissue, the first data and the second data corresponding to the second 3D data;

integrate the first data and the second data to generate the graphical model.

19. The one or more machine-readable storage media of claim 13, wherein displaying comprises displaying a position of the simulated soft tissue at specified times following surgery, the specified times being defined by recorded data.

20. The one or more machine-readable storage media of claim 13, wherein the simulated soft tissue moves in accordance with a ratio of skin movement to bone movement, the ratio being defined based on a location of the soft tissue as it relates to craniofacial anatomy.

21. The one or more machine-readable storage media of claim 13, further comprising instructions that are executable to cause one or more processing devices to:

maintain a database containing the first 3D data, the database being in the memory;

obtain updates to the database; and incorporate the updates into the database to thereby produce an updated database, the updates comprising additional 3D data for additional subjects that specifies how soft tissue moves over time in response to movement of underlying bone.

22. The one or more machine-readable storage media of claim 21, wherein obtaining the updates comprises receiving the updates over a computer network.

23. The one or more machine-readable storage media of claim 21, further comprising instructions to provide only physicians who have obtained subscriptions with access to the updated database.

24. The one or more machine-readable storage media of claim 13, further comprising instructions that are executable to cause one or more processing devices to:

predict, using at least some of the first 3D data, movement of soft tissue of the second subject over time in response to movement of an underlying structure that is not bone.

25. An apparatus comprising:

memory to store, for first subjects, first three-dimensional (3D) data identifying movement of soft tissue of a face in response to movement of underlying bone; and one or more processing devices to predict, using at least some of the first 3D data, movement of soft tissue of a face of a second subject over time in response to movement of underlying bone, the first subjects and the second subject comprising different people;

wherein predicting movement of the soft tissue of the face of the second subject is performed by the one or more processing devices and comprises:

generating a graphical model of the second subject using second 3D data for soft tissue and underlying bone of the second subject, the graphical model simulating the soft tissue and the underlying bone for the second subject to thereby display simulated soft tissue and simulated underlying bone;

moving the simulated underlying bone on the graphical model; and displaying, via the graphical model, movement of the simulated soft tissue in response to movement of the simulated underlying bone, the at least some of first 3D data being used to predict movement of the simulated soft tissue for the second subject, wherein the graphical model is displayed via a computer.

26. The apparatus of claim 25, wherein the first 3D data takes into account one or more biophysical properties that affect movement of the soft tissue, the one or more biophysical properties including pliability of the skin, thickness of the soft tissue, and scar tissue associated with the soft tissue.

27. The apparatus of claim 25, wherein the first 3D data takes into account an amount of time that lapses between movement of the underlying bone and movement of the soft tissue.

28. The apparatus of claim 25, wherein displaying comprises displaying positions of the simulated soft tissue at different times following movement of the underlying bone.

29. The apparatus of claim 25, wherein movement of the underlying bone is a result of craniofacial surgery performed on the second subject.

30. The apparatus of claim 25, wherein generating the graphical model of the second subject comprises:

obtaining imaging scans for the second subject, the imaging scans relating to craniofacial anatomy of the second subject;

obtaining first data and second data from the imaging scans, the first data corresponding to bone and the second data corresponding to soft tissue, the first data and the second data corresponding to the second 3D data;

integrating the first data and the second data to generate the graphical model.

31. The apparatus of claim 25, wherein displaying comprises displaying a position of the simulated soft tissue at specified times following surgery, the specified times being defined by recorded data.

32. The apparatus of claim 25, wherein the simulated soft tissue moves in accordance with a ratio of skin movement to bone movement, the ratio being defined based on a location of the soft tissue as the location relates to craniofacial anatomy.

33. The apparatus of claim 25, wherein the one or more processing devices are programmed to:

maintain a database containing the first 3D data, the database being in the memory;

obtain updates to the database; and incorporate the updates into the database to thereby produce an updated database, the updates comprising additional 3D data for additional subjects that specifies how soft tissue moves over time in response to movement of underlying bone.

34. The apparatus of claim 33, wherein obtaining the updates comprises receiving the updates over a computer network.

35. The apparatus of claim 33, further comprising providing only physicians who have obtained subscriptions with access to the updated database.

36. The apparatus of claim 25, wherein the one or more processing devices are programmed to:

predict, using at least some of the first 3D data, movement of soft tissue of the second subject over time in response to movement of an underlying structure that is not bone.

* * * * *

UNITED STATES PATENT AND TRADEMARK OFFICE
CERTIFICATE OF CORRECTION

| | | |
|---|---|---|
| PATENT NO. | : 7,953,260 B2 | Page 1 of 1 |
| APPLICATION NO. | : 11/450651 | |
| DATED | : May 31, 2011 | |
| INVENTOR(S) | : Jeffrey Weinzweig and Darren Smith | |

It is certified that error appears in the above-identified patent and that said Letters Patent is hereby corrected as shown below:

Column 11, Claim 1, Line 13;
Delete "data" and insert --data,--

Column 12, Claim 13, Line 32:
Delete "of second" and insert --of the second--

Signed and Sealed this
Twenty-eighth Day of February, 2012

David J. Kappos
*Director of the United States Patent and Trademark Office*